United States Patent
Youssefi

(10) Patent No.: US 9,393,155 B2
(45) Date of Patent: Jul. 19, 2016

(54) SYSTEM AND METHOD FOR POSTOPERATIVE CAPSULAR BAG CONTROL

(75) Inventor: Gerhard Youssefi, Landshut (DE)

(73) Assignee: TECHNOLAS PERFECT VISION GMBH, Munich (DE)

( * ) Notice: Subject to any disclaimer, the term of this patent is extended or adjusted under 35 U.S.C. 154(b) by 1159 days.

(21) Appl. No.: 13/338,872

(22) Filed: Dec. 28, 2011

(65) Prior Publication Data

US 2013/0172861 A1 Jul. 4, 2013

(51) Int. Cl.
*A61N 5/06* (2006.01)
*A61F 9/008* (2006.01)

(52) U.S. Cl.
CPC ..... *A61F 9/00825* (2013.01); *A61F 2009/0087* (2013.01); *A61F 2009/00851* (2013.01); *A61F 2009/00887* (2013.01)

(58) Field of Classification Search
CPC ........... A61F 9/008; A61F 2009/00872; A61F 2009/00897; A61F 2009/00863; A61F 9/00825
USPC .......................................................... 606/4
See application file for complete search history.

(56) References Cited

U.S. PATENT DOCUMENTS

| | | | |
|---|---|---|---|
| 5,098,426 A | 3/1992 | Sklar et al. | |
| 6,751,033 B2 | 6/2004 | Goldstein et al. | |
| 7,027,233 B2 | 4/2006 | Goldstein et al. | |
| 7,655,002 B2 | 2/2010 | Myers | |
| 8,231,221 B2 | 7/2012 | Donitzky et al. | |
| 2002/0173778 A1 | 11/2002 | Knopp et al. | |
| 2002/0198516 A1 | 12/2002 | Knopp et al. | |
| 2009/0149841 A1 | 6/2009 | Kurtz | |
| 2010/0082017 A1 | 4/2010 | Zickler et al. | |
| 2010/0324542 A1* | 12/2010 | Kurtz ..................... | A61F 9/008 606/6 |

FOREIGN PATENT DOCUMENTS

| | | |
|---|---|---|
| EP | 2392293 A1 | 6/2010 |
| WO | 2007143111 A2 | 12/2007 |
| WO | 2008112292 A1 | 9/2008 |
| WO | 2012050622 A2 | 4/2012 |

OTHER PUBLICATIONS

PCT International Search Report, Application No. PCT/IB2012/002750, Dec. 19, 2012.

* cited by examiner

*Primary Examiner* — Amanda Patton
*Assistant Examiner* — Philip C Edwards
(74) *Attorney, Agent, or Firm* — Nydegger & Associates

(57) ABSTRACT

In accordance with the present invention, a system and method are provided for controlling postoperative shrinkage of the capsular bag, after the lens has been removed from the capsular bag. The purpose is to establish a proper optical alignment for a prosthetic Intraocular Lens (IOL). Included in the system are a laser unit for generating a laser beam, a detector for creating an image of the prosthetic IOL in the capsular bag, and a computer for evaluating the image to determine an alignment difference between the IOL axis and a defined axis of the eye. The computer is also used for guiding the laser beam to alter selected tissue in the eye, to thereby influence postoperative shrinkage of the capsular bag and minimize any potential alignment difference between the IOL axis and the defined axis of the eye during capsular bag shrinkage.

20 Claims, 1 Drawing Sheet

SYSTEM AND METHOD FOR POSTOPERATIVE CAPSULAR BAG CONTROL

FIELD OF THE INVENTION

The present invention pertains generally to ophthalmic laser surgery. More particularly, the present invention pertains to systems and methods for the postoperative positioning of a prosthetic Intraocular Lens (IOL) in a capsular bag (i.e. capsule), after the natural lens has been removed from the capsular bag during a cataract procedure. The present invention is particularly, but not exclusively, useful as a system and method for performing postoperative surgical laser alterations on the capsular bag by Laser Induced Optical Breakdown (LIOB), to thereby influence the proper alignment of the prosthetic Intraocular Lens (IOL) in the capsular bag.

BACKGROUND OF THE INVENTION

In a typical cataract surgery, the capsular bag that is holding the crystalline lens of the eye is compromised, and the lens is then removed. A prosthetic Intraocular Lens (IOL) is then inserted into the capsular bag. To make this exchange, a hole (i.e. a capsulorhexis, or so-called "Rhexis") is created on the anterior surface of the capsular bag. The objective of all of this is that the implanted prosthetic IOL will function in the stead of the removed cataractous lens. For this to happen, the optical axis of the prosthetic IOL (hereinafter the "IOL axis") needs to be properly aligned with a defined axis of the eye.

It is well known that, after the removal of the cataractous lens, the capsular bag will shrink during the weeks immediately following surgery. From a surgical perspective, this reality poses several different possibilities. For one, capsular bag shrinkage may cause the IOL axis of the prosthetic IOL to become somehow misaligned. Such a misalignment can happen for various reasons, and it must necessarily be avoided. On the other hand, the fact there will be capsular bag shrinkage can be helpful, if the shrinkage is controlled to establish a proper alignment.

One way to control the postoperative capsular bag is to influence its shrinkage pattern. In particular, it is known that selectively weakening tissues of the capsular bag can be useful for this purpose. It is also well known that ocular tissues can be weakened by performing Laser Induced Optical Breakdown (LIOB) techniques. Before doing this, however, it is necessary to determine the nature and the extent of the required shrinkage control. In the context of postoperative cataract surgery, this requires an evaluation of the condition of the capsular bag, along with a determination of the orientation of the IOL axis of the implanted prosthetic IOL. The effect of capsular bag shrinkage can then be reasonably predicted.

In light of the above, it is an object of the present invention to provide a system and method for performing LIOB on tissue of a capsular bag in order to influence shrinkage of the bag after cataract surgery. Specifically, this is done for the purpose of properly orienting a prosthetic IOL on a defined axis of the eye, while the prosthetic IOL is positioned in the capsular bag. Another object of the present invention is to surgically influence capsular bag shrinkage in response to optical images of a prosthetic IOL in the capsular bag. Yet another object of the present invention is to provide a system and method for postoperatively aligning the IOL axis of a prosthetic IOL with a defined axis of an eye, by influencing the shrinkage of the eye's capsular bag. Still another object of the present invention is to provide a system and method for the postoperative alignment of an IOL which is simple to use, is easy to implement, and is relatively cost effective.

SUMMARY OF THE INVENTION

In accordance with the present invention, a system and method are provided for altering the eye to compensate for the adverse effects of an IOL misalignment that may result from postoperative shrinkage of the capsular bag in the eye. It happens that, after a lens has been removed from its capsular bag during a cataract surgery, the capsular bag will shrink. Sometimes, it happens that this shrinkage will adversely affect the optical orientation of the prosthetic Intraocular Lens (IOL) that has been inserted into the capsular bag. The most common causes for such an adverse effect include: 1) an unbalanced force distribution on the capsular bag; 2) a decentered capsulorhexis; and 3) an unexpected rupture of the capsular bag. Regardless of the particular cause, the present invention is provided to control postoperative shrinkage of the capsular bag. For the present invention, this is done by using Laser Induced Optical Breakdown (LIOB) techniques to alter the shrinkage pattern of the capsular bag. Importantly, this is done in a manner that establishes a proper alignment of the optical axis of the prosthetic IOL (i.e. the IOL axis) with a predefined axis of the eye. In this case, the defined axis of the eye can be defined as being either a line-of-sight axis, a visual axis, a pupillary axis, a compromise axis or any other geometrically or anatomically defined axis.

Structurally, the system of the present invention includes a laser unit for generating a laser beam. Also included is a detector for creating an image of the prosthetic IOL after it has been postoperatively positioned inside the capsular bag. Connected to both the laser unit and the detector is a computer. In its operation, the computer is used for evaluating the image that is created by the detector, and for guiding the laser unit in response to this evaluation of the image.

The laser unit of the present invention is preferably of a type that is capable of generating a pulsed femtosecond laser beam. Importantly, this laser beam must be capable of performing Laser Induced Optical Breakdown (LIOB) to alter tissue of the capsular bag, and of the zonular fibers that are connected to the capsular bag. In particular, it is envisioned that the LIOB performed for the present invention will result in cuts and/or punctures of the tissue of the capsular bag. Further, these cuts and/or punctures may be either symmetrical or asymmetrical.

The detector that is used for the present invention must be of a type that is capable of in situ imaging the capsular bag of an eye. Importantly, the detector must be capable of imaging the prosthetic IOL that is inserted into the capsular bag during a surgical procedure. For the present invention, the detector will preferably be an Optical Coherence Tomography (OCT) device.

As indicated above, the computer is used to evaluate the positioning of the prosthetic IOL while it is in the capsular bag. This evaluation of the image is effectively two-fold. For one, image evaluation is done to determine any alignment difference there may be between the IOL axis of the prosthetic IOL and a defined axis of the eye. For another, the image is evaluated to predict the postoperative shrinkage pattern of the capsular bag. For this second purpose, the computer selectively evaluates several considerations. These include: 1) the force distribution that is imposed by the capsular bag on the prosthetic IOL; 2) the location of the capsulorhexis through the capsular bag [i.e. the hole that is created in the capsular bag for removal of the lens and subsequent insertion of the prosthetic IOL]; and 3) any unexpected rupture of the capsular bag. For the present invention, this image evaluation can be done in accordance with a prepared computer program and can be done at any time, as needed.

Once there has been an evaluation of the optical axis alignment, and a prediction of the shrinkage pattern, the computer is used to guide the laser unit to alter selected tissue in the eye. Specifically, this is done with LIOB cuts and/or punctures of the capsular bag or zonular fibers for the purpose of influencing shrinkage of the capsular bag. The objective here is to thereby establish a proper optical alignment of the IOL axis with the defined optical axis of the eye. For the present invention, the LIOB cuts and/or punctures may be the result of radial cuts, cylindrical cuts, line cuts, curved cuts or any combination of the above.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
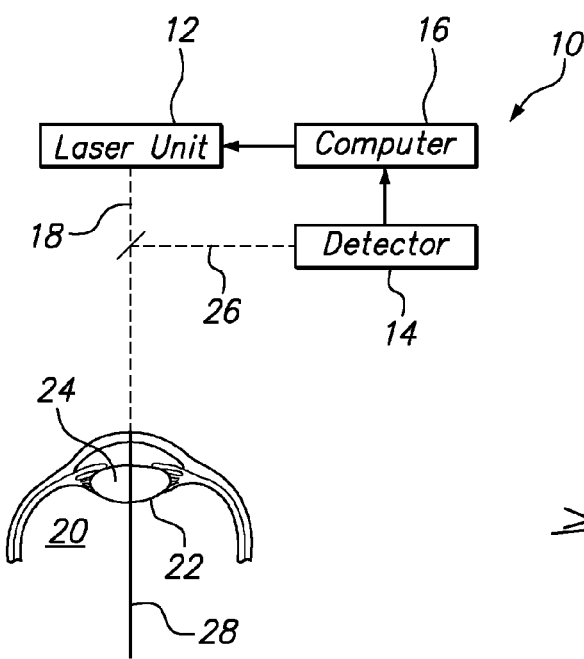
FIG. 1 is a schematic diagram of system components shown in an operational configuration with an eye, with the eye shown in cross section.

Referring initially to FIG. 1 a system for establishing a proper optical alignment of an eye after cataract surgery is shown and is generally designated 10. As shown, the system 10 includes a laser unit 12, a detector 14, and a computer 16. In detail, the laser unit 12 is preferably a so-called "femtosecond" laser which can generate a pulsed laser beam 18 that includes pulses with durations less than about 500 femtoseconds. Importantly, the laser beam 18 must be able to perform a Laser Induced Optical Breakdown (LIOB) of ophthalmic tissue in the eye 20. More specifically, for purposes of the present invention, it is important that the laser unit 12 be able to perform LIOB on the tissue of the capsular bag 22 that surrounds the crystalline lens 24 of the eye 20. It is also important that the detector 14 be able to use an imaging beam 26 for the creation of a three dimensional image of the capsular bag 22. Preferably, the detector 14 will incorporate Optical Coherence Tomography (OCT) techniques. For these purposes, it is envisioned that both the laser beam 18 from the laser unit 12, as well as the imaging beam 26 from the detector 14, will be directed toward the eye 20 either along, or substantially parallel to, a predefined axis 28 for the eye 20. For purposes of the present invention, the predefined axis 28 may be a line-of-sight axis, a visual axis, a pupillary axis, a compromise axis or some other geometrically defined axis.

Figure 2:
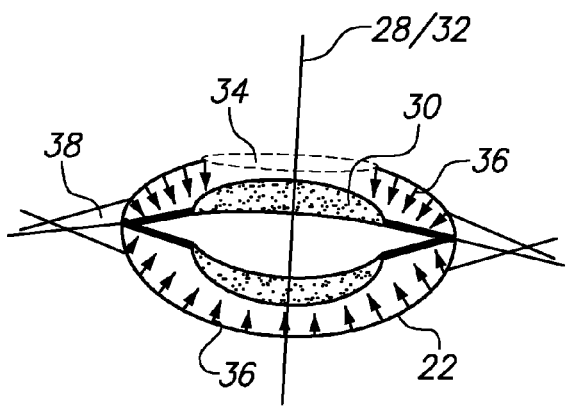
FIG. 2 is a cross section view of an IOL positioned in the capsular bag of the eye, after cataract surgery, showing shrinkage forces acting on the capsular bag.
Figure 3:
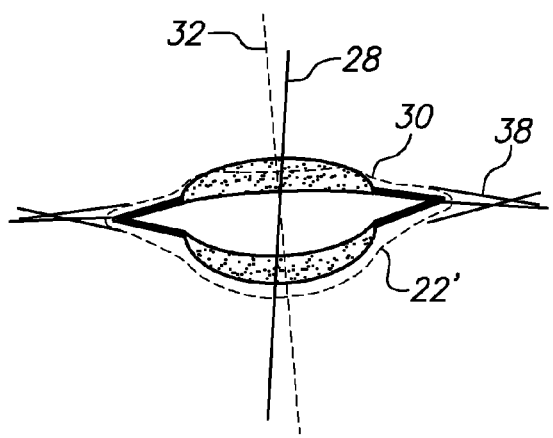
FIG. 3 is a view of the IOL shown in FIG. 2 with the IOL in an optical misalignment due to capsular bag shrinkage.

In FIG. 2, an Intraocular Lens (IOL) 30 is shown positioned inside the capsular bag 22 of eye 20, in place of the crystalline lens 24 that has been removed during a cataract surgery. Importantly, the IOL 30 will have its own optical axis (hereinafter referred to as IOL axis 32). And, it is an important result of the cataract surgery that, after the IOL 30 has been inserted through a surgical opening in the capsular bag 22 (commonly referred to as a Rhexis 34), the IOL axis 32 will be oriented substantially coaxial with the predefined axis 28 of the eye 20. As is well known to the skilled artisan, however, shrinkage forces (represented by arrows 36 in FIG. 2) will be exerted by the capsular bag 22 against the IOL 30 for several months following surgery. The consequence here is that the capsular bag 22 will shrink to a configuration for the capsular bag 22' shown by a dashed line in FIGS. 3 and 4. Moreover, for several different reasons, these shrinkage forces 36 can cause the IOL axis 32 to become misaligned with the predefined axis 28 (see FIG. 3). For example, the Rhexis 34 may have been decentered during the surgery, with a consequent asymmetry of remaining tissue of the capsular bag 22. Or, perhaps, the zonular fibers 38 around the periphery of the capsular bag 22 may have been asymmetrically weakened during the surgery. Possibly, the capsular bag 22 may itself have been torn or ruptured during the surgery. In any event, an asymmetrical shrinkage of the capsular bag 22, with a resultant misalignment of the IOL axis 32 relative to the predefined axis 28, is to be avoided.

Figure 4:
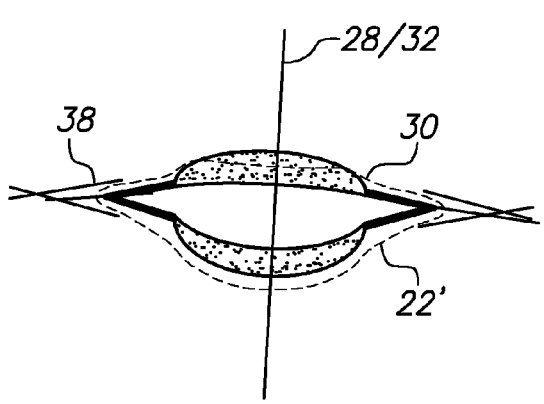
FIG. 4 is a view of the IOL shown in FIG. 2 with the IOL in a proper, postoperative, optical alignment.

As envisioned by the present invention, the detector 14 is used to postoperatively image the IOL 30, in situ, in the capsular bag 22. Importantly, this imaging is used to determine the orientation of the IOL axis 32 relative to the predefined axis 28, and to thereby identify any deviations from a coaxial alignment. If there are any deviations, appropriate LIOB alterations of the capsular bag 22 can be made by the laser unit 12 to control the shrinkage of capsular bag 22. To do this, the present invention envisions the use of symmetrical or asymmetrical cuts and/or punctures into the capsular bag 22 and/or the zonular fibers 38. These cuts and/or punctures, along with other possible tissue removal, can be made essentially anywhere through the capsular bag 22. Further, the cuts can be either radial cuts or cylindrical cuts. In the event, it is important that the capsular bag 22 be structurally altered to shrink into a configuration that will establish a proper coaxial alignment of the IOL axis 32 with the predefined axis 28 of eye 20 as shown in FIG. 4.

While the particular System and Method for Postoperative Capsular Bag Control as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for controlling postoperative shrinkage of a capsular bag of an eye to establish a proper optical alignment for a prosthetic Intraocular Lens (IOL) in the capsular bag, the system comprising:

a laser unit for generating a laser beam;

a detector for creating an image of the prosthetic IOL and the capsular bag when the prosthetic IOL is postoperatively positioned inside the capsular bag, wherein the prosthetic IOL defines a prosthetic IOL axis; and a computer connected to the laser unit, and to the detector, for evaluating the image to determine an alignment difference between the prosthetic IOL axis and a predefined axis of the eye, and for guiding the laser unit to alter selected tissue in the eye to influence shrinkage of the capsular bag to minimize the alignment difference and establish a proper alignment of the prosthetic IOL axis with the predefined axis of the eye.

2. A system as recited in claim 1 wherein the laser unit includes components for generating a pulsed femtosecond laser beam.

3. A system as recited in claim 1 wherein the detector is an Optical Coherence Tomography (OCT) device.

4. A system as recited in claim 1 wherein the alteration of selected tissue is accomplished by performing Laser Induced Optical Breakdown (LIOB) on the tissue.

5. A system as recited in claim 4 wherein the tissue to be altered is selected from a group including tissue of the capsular bag and zonular fibers.

6. A system as recited in claim 4 wherein LIOB results in tissue alterations selected from a group including cuts and punctures of the tissue of the capsular bag.

7. A system as recited in claim 6 wherein the cuts and punctures are asymmetrical.

8. A system as recited in claim 6 wherein the cuts and punctures are selected from a group including radial cuts and cylindrical cuts.

9. A system as recited in claim 1 wherein the computer evaluates the image with considerations for a force distribution imposed by the capsular bag on the prosthetic IOL, a location of capsulorhexis through the capsular bag on the prosthetic IOL, and an unexpected rupture of the capsular bag.

10. A system as recited in claim 1 wherein the predefined axis of the eye is selected from a group including a line-of-sight axis, a visual axis, a pupillary axis, a compromise axis and a geometrically defined axis.

11. A method for controlling a postoperative shrinkage of a capsular bag of an eye to establish a proper optical alignment for a prosthetic Intraocular Lens (IOL) positioned in the capsular bag, the method comprising the steps of:
 defining an axis for the eye;
 providing a prosthetic IOL having a defined prosthetic IOL axis;
 inserting the prosthetic IOL into a capsular bag in an eye;
 creating an image of the prosthetic IOL in the capsular bag;
 using the image to measure a difference in alignment between the prosthetic IOL axis of the prosthetic IOL and the defined axis of the eye;
 evaluating the capsular bag in situ; and
 altering tissue in the eye in response to the evaluating step, to influence shrinkage of the capsular bag for minimizing the difference measured in the using step.

12. A method as recited in claim 11 wherein the creating step is accomplished using an Optical Coherence Tomography (OCT) device.

13. A method as recited in claim 11 wherein the altering step is accomplished by performing Laser Induced Optical Breakdown (LIOB) on the tissue selected from a group including tissue of the capsular bag and zonular fibers.

14. A method as recited in claim 13 wherein LIOB results in tissue alterations selected from a group including cuts and punctures of the tissue of the capsular bag, wherein the cuts and punctures are asymmetrical, and wherein the cuts and punctures are selected from a group including radial cuts and cylindrical cuts.

15. A method as recited in claim 13 wherein the evaluating step involves considerations for a force distribution imposed by the capsular bag on the prosthetic IOL, a location of capsulorhexis through the capsular bag on the prosthetic IOL, and an unexpected rupture of the capsular bag.

16. A method as recited in claim 11 wherein the defining step is accomplished by selecting the defined axis of the eye from a group including a line-of-sight axis, a visual axis, a pupillary axis, a compromise axis and a geometrically defined axis.

17. A computer program product for controlling a postoperative shrinkage of a capsular bag of an eye to establish a proper optical alignment for a prosthetic Intraocular Lens (IOL) positioned in the capsular bag, comprising program sections for respectively: defining an axis for the eye; creating an image of the prosthetic IOL in the capsular bag using an Optical Coherence Tomography (OCT) device wherein the prosthetic IOL has a defined prosthetic IOL axis; using the image to measure a difference in alignment between the prosthetic IOL axis of the prosthetic IOL and the defined axis for the eye; evaluating the capsular bag; and altering tissue in the eye in response to the evaluation of the capsular bag, to influence shrinkage of the capsular bag for minimizing the measured difference in alignment.

18. A computer program product as recited in claim 17 further comprising a program section for considering a force distribution imposed by the capsular bag on the prosthetic IOL, a location of capsulorhexis through the capsular bag on the prosthetic IOL, and an unexpected rupture of the capsular bag.

19. A computer program product as recited in claim 17 further comprising a program section for selecting the defined axis of the eye from a group including a line-of-sight axis, a visual axis, a pupillary axis, a compromise axis and a geometrically defined axis.

20. A computer program product as recited in claim 17 further comprising a program section for performing Laser Induced Optical Breakdown (LIOB) on the tissue, wherein the tissue is selected from a group including tissue of the capsular bag and zonular fibers, and further wherein LIOB results in tissue alterations selected from a group including cuts and punctures of the tissue of the capsular bag and are selected from a group including radial cuts and cylindrical cuts.

* * * * *